United States Patent
Stoop

[11] Patent Number: 5,861,011
[45] Date of Patent: Jan. 19, 1999

[54] PACEMAKER WITH AUTOMATIC LOWER RATE LIMIT DROP

[75] Inventor: Gustaaf A. P. Stoop, Dieren, Netherlands

[73] Assignee: Vitatron Medical, B.V., Dieren, Netherlands

[21] Appl. No.: 800,413

[22] Filed: Feb. 14, 1997

[51] Int. Cl.$^6$ .................................................. A61N 1/365
[52] U.S. Cl. ....................................................... 607/25
[58] Field of Search .............................. 607/17, 18, 25, 607/19

[56] References Cited

U.S. PATENT DOCUMENTS

| | | |
|---|---|---|
| 4,228,803 | 10/1980 | Rickards . |
| 4,305,396 | 12/1981 | Wittkampf et al. . |
| 4,782,836 | 11/1988 | Alt ............................................. 607/19 |
| 4,922,930 | 5/1990 | Adkins et al. . |
| 4,972,834 | 11/1990 | Begemann et al. . |
| 5,143,065 | 9/1992 | Adkins et al. . |
| 5,282,839 | 2/1994 | Roline et al. .............................. 607/19 |

OTHER PUBLICATIONS

U. Stierle et al., "Die zirkadiane Stim–T–Rhythmik als eine Grundlage des automatisierten QT–Schrittmachers," Herz–Schrittmacher, 9:135–143 (1989) [Summary paragraph on p. 135 is in English].

*Primary Examiner*—Jeffrey R. Jastrzab
*Attorney, Agent, or Firm*—Woodcock Washburn Kurtz Mackiewicz & Norris LLP

[57] ABSTRACT

There is provided an implanted pacemaker having a system and method for determining a measure of the circadian rhythm of a patient and adjusting the pacemaker nighttime setting of lower rate limit to correspond to the determined circadian rhythm. In a preferred embodiment, the circadian rhythm is determined by examining daily variations in QT interval. In a first QT embodiment of the invention, when QT interval becomes longer than a parameter QT_sleep, which represents a value associated with patient nighttime, the LRL is dropped to a night value and maintained at such value for a predetermined duration. In another embodiment, the start of night LRL is determined as a function of when QT interval becomes longer than a sleep value for a predetermined elapsed time, and LRL is changed back to a day value when QT interval drops back down to a shorter value than the sleep value and stays there for an elapsed period of time. In yet another algorithm in accordance with this invention, the sleep value of QT interval is adapted so that the night period when QT interval is longer than the sleep value more closely corresponds to desired time of sleep, and the start of night LRL and the start of Day LRL are shifted to correspond to the detected night period. Additionally, other pacing parameters such as the escape interval hysteresis value may be varied based on determinations of the circadian rhythm.

19 Claims, 9 Drawing Sheets

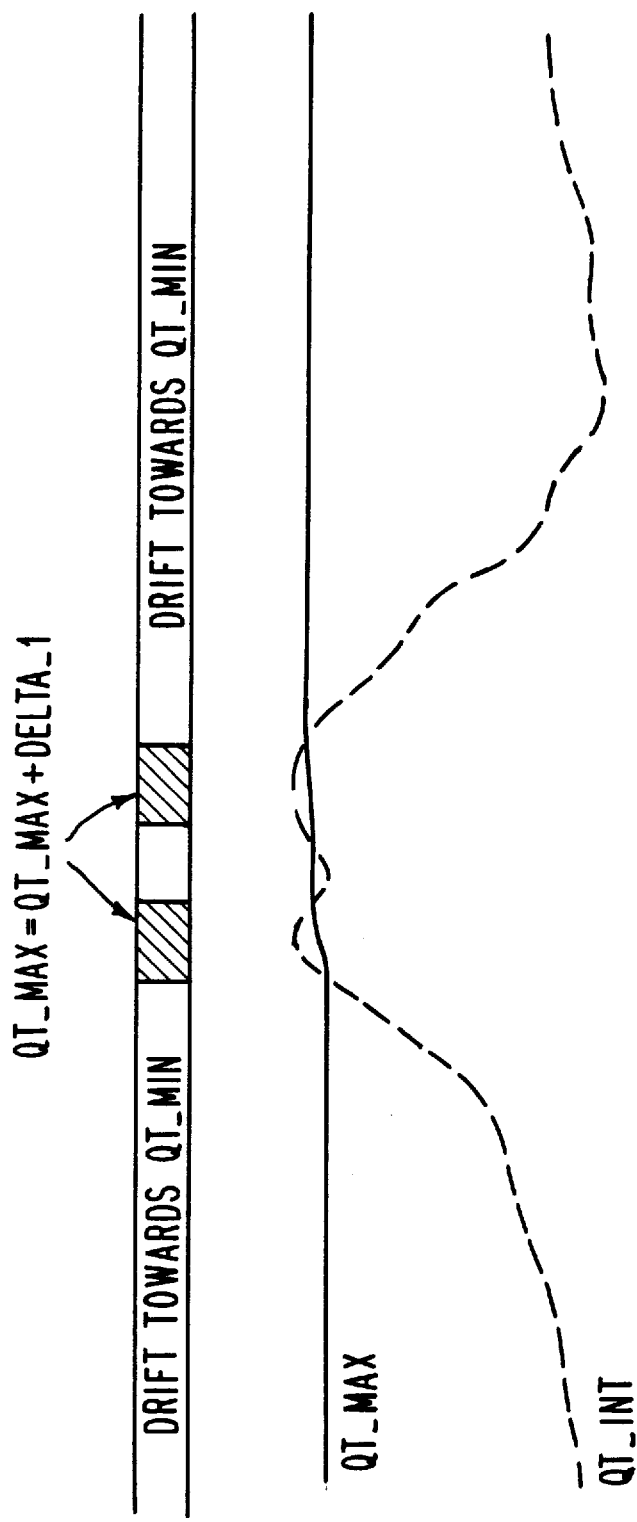

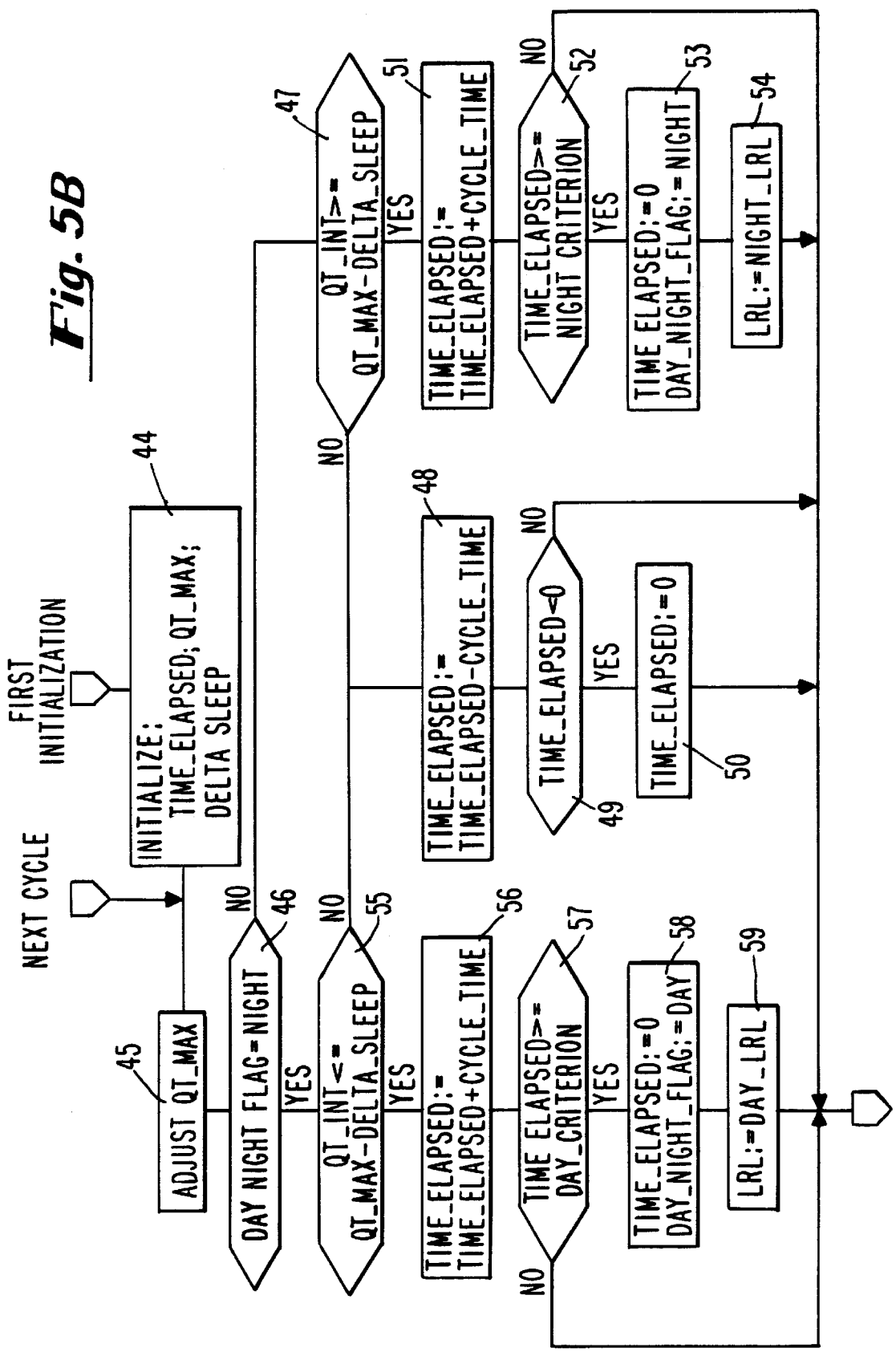

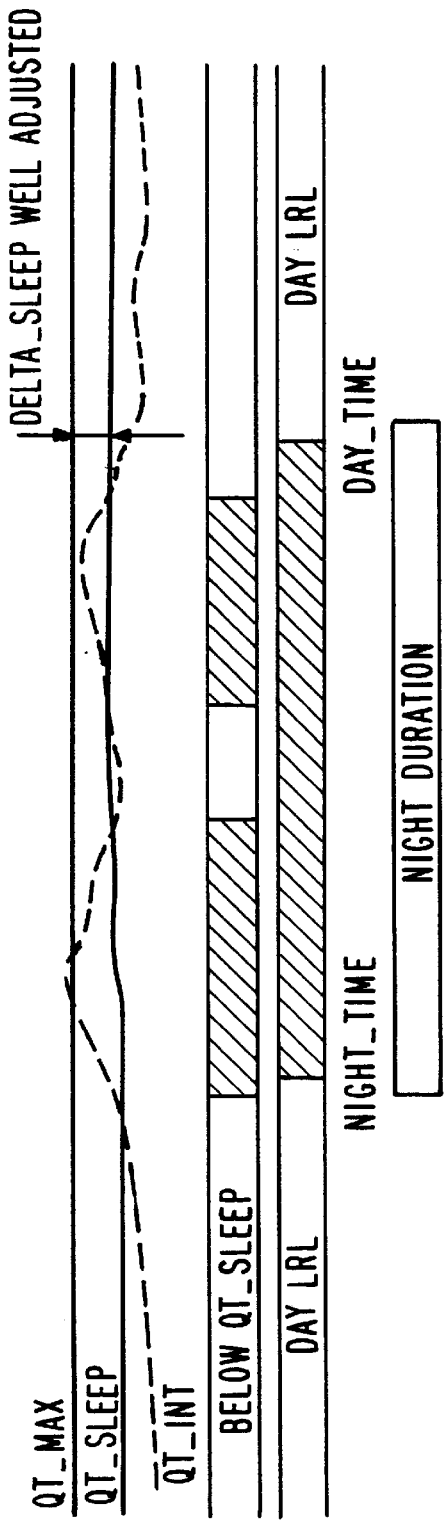
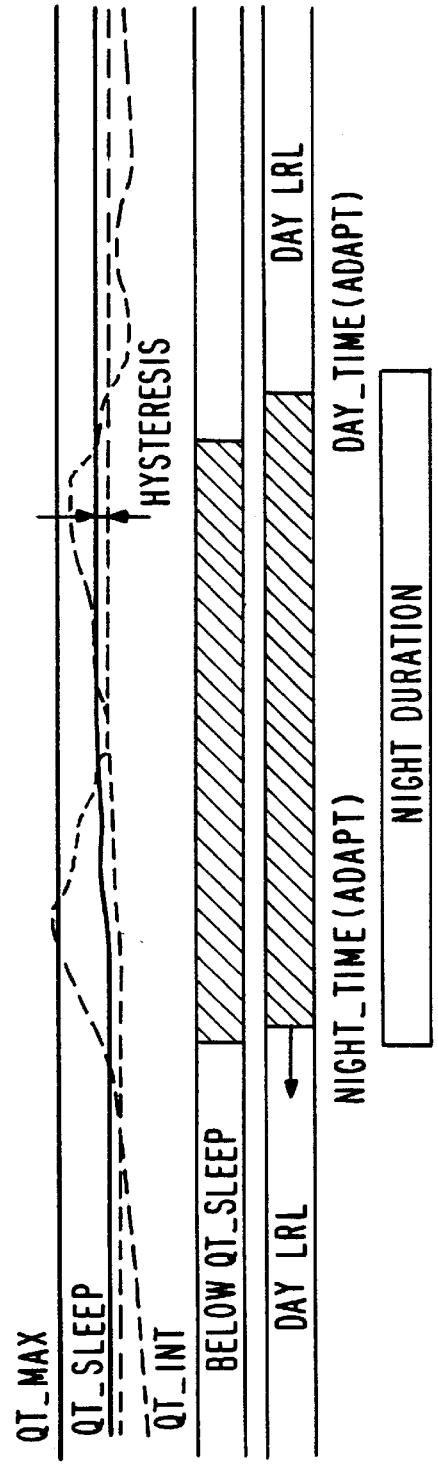
Fig. 6A
Fig. 6B

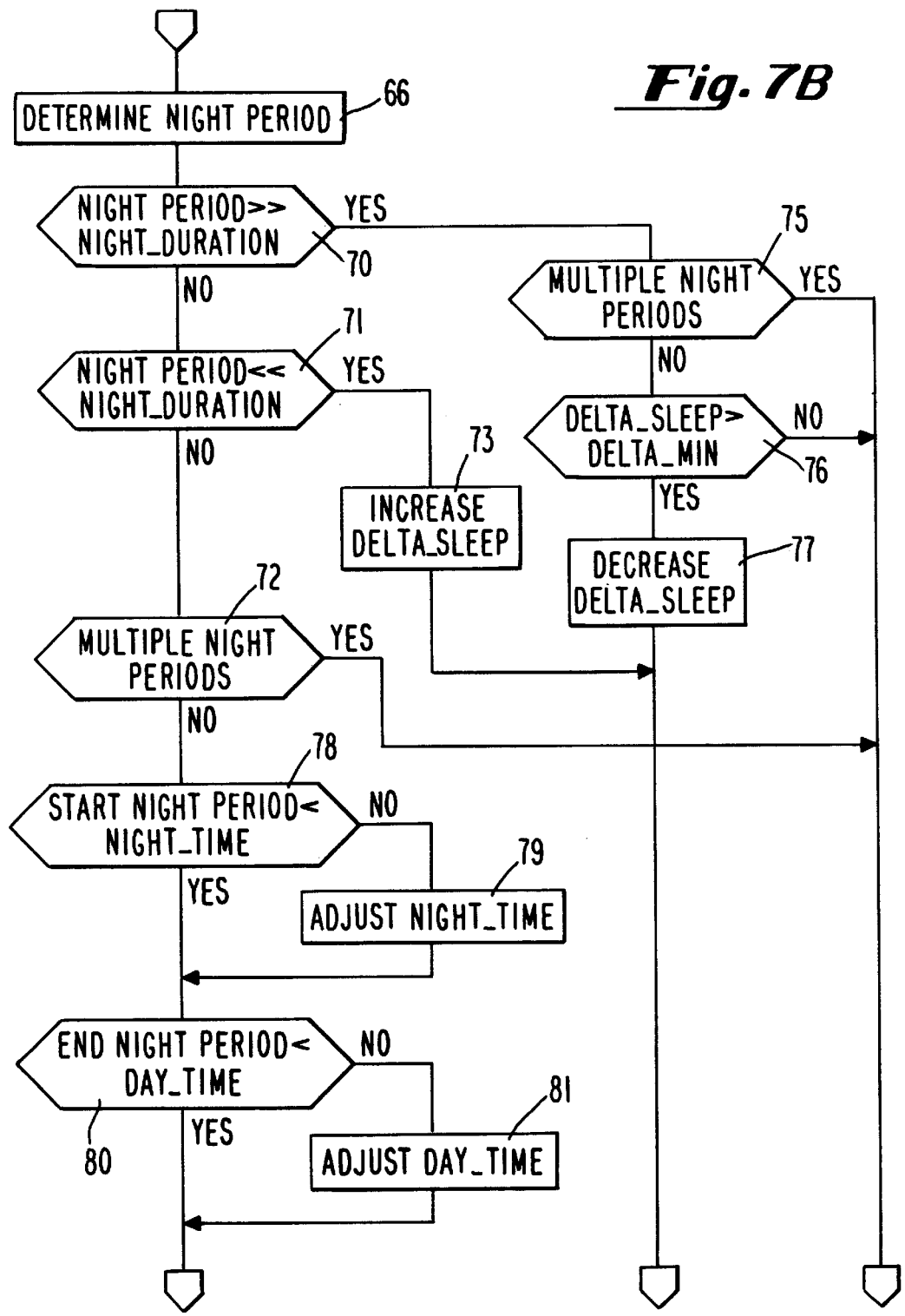

PACEMAKER WITH AUTOMATIC LOWER RATE LIMIT DROP

FIELD OF THE INVENTION

This invention relates to cardiac pacemakers and, more particularly, implantable rate responsive pacemakers of the type having the feature of dropping the lower rate limit at nighttime.

BACKGROUND OF THE INVENTION

Current generation rate responsive implantable pacemakers generally use a programmable, but fixed lower rate limit (LRL). As the term indicates, the lower rate limit establishes a low limit to the pacing rate for a rate responsive pacemaker, to ensure that the pacing rate does not drop to an undesirable brady level. It is desirable to enable a lower pacing rate during nighttime than during daytime, for physiological reasons; during the night, patient metabolism drops and a lower rate is more natural and physiological. Further, as is well known, provision of a lower rate at night means few delivered pacing pulses over an extended period of time, and thus a substantial savings in battery energy. Some current pacemakers provide for automatic drop of LRL at night. Such automatic rate drop at night can be provided simply by an internal clock, or by a detected parameter which indicates low patient activity or metabolism, from which the pacemaker can conclude nighttime.

A problem inherent in the usual form of rate drop at night is that the pacemaker does not follow the patient's circadian variation. Circadian variations may occur due to changes in the individual's state of health or general constitution, as well as summer/winter time transitions and travel to different time zones. For whatever the reason the circadian variations, it is desirable that the pacemaker be able to track and adjust to these variations and changing sleep patterns. Accordingly, what is needed in the art is a pacemaker which is able to continuously sense one or more biological parameters which accurately reflect the patient's circadian variation, and continually adapt the timing for switching between daytime LRL and nighttime LRL to best follow the circadian variations. In the preferred embodiment of this invention, use is made of the observation that daily variations in QT interval (QT) are an accurate reflection of circadian variations. At nighttime, the value of QT rises toward a daily maximum, and recognition of this enables a determination of patient nighttime suitable for lowering LRL.

SUMMARY OF THE INVENTION

There is provided a system and method for tracking the circadian rhythm of a patient with an implantable pacemaker, involving continuously determining the slow changes of a parameter value, e.g., QT interval, which provide a measure of variations of the circadian rhythm. Moving maximum daily values of QT are determined, as well as a sleep value of QT which serves as a threshold variable for determining nighttime. In a preferred algorithm, the sleep value of QT is adjusted to track changes in the circadian rhythm. One or more criteria affecting pacemaker rate response, such as low rate limit, can be adjusted to a nighttime value based primarily on when QT interval is determined to exceed the sleep value, thus indicating that the patient has commenced rest indicative of nighttime, and maintained for a predetermined sleep duration. Alternately, the pacemaker can define nighttime variables as the start of the night and end of the night, and adjust these two variables on a daily basis. The variable and shifting period between these variables reflects the actual shifting of the patient's sleep condition. In this alternate embodiment, the lower LRL (or sleep value of LRL) is in effect during this period.

BRIEF DESCRIPTION OF THE DRAWINGS

FIG. 2 is a diagram illustrating the circadian variation in the QT interval, and the parameter QT_max.

FIG. 5B is a flow diagram of a pacemaker algorithm for determining the night LRL in accordance with the arrangement illustrated in FIG. 3B, where night LRL is determined as a function of QT_sleep, night_criterion and day_criterion.

FIG. 6A is a diagram illustrating determination of daytime and nighttime LRL by daily shifting of the parameter QT_sleep and parameters night_time and day_time, to adjust the lower LRL to patient conditions; and FIG. 6B is a diagram similar to FIG. 6A, where a hysteresis value is added to the parameter QT_sleep so as to optimize the determination of actual patient nighttime where QT is above QT_sleep, or night_period.

FIG. 7B is a flow diagram of an algorithm in accordance with this invention for making a daily evaluation of the pacemaker-determined nighttime relative to the patient's actual night period, and for adapting night LRL to better match the patient when there is a clearly determined circadian pattern.

DESCRIPTION OF THE PREFERRED EMBODIMENTS

Figure 1:
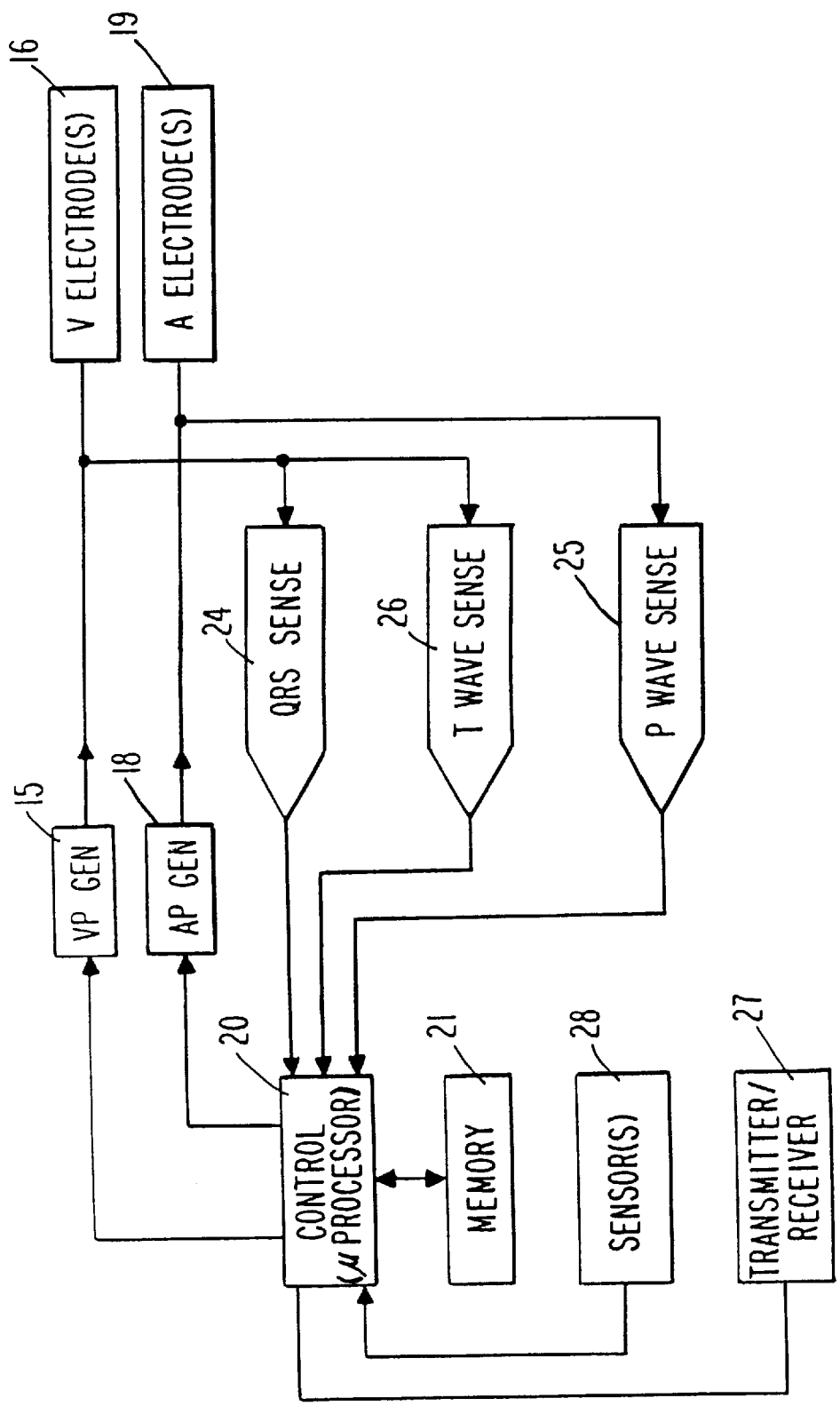
FIG. 1 is a simplified block diagram of an implantable pacemaker as used in this invention.

Referring now to FIG. 1, there is shown a simplified block diagram of the primary components of a pacemaker as used in the system and method of this invention. Although a dual chamber pacemaker is illustrated for completeness, it is to be understood that the invention is equally applicable to single or dual chamber rate responsive pacemakers. A ventricular pace generator is illustrated at 15 for generating and delivering ventricular pace pulses under control of control unit 20, in a known fashion. The ventricular pace pulses are delivered to one or more ventricular electrodes illustrated at 16. Likewise an atrial pace generator is illustrated at 18, which generates atrial pace pulses under control block 20 and delivers the atrial pace pulses to one or more atrial electrodes as illustrated at 19. Sense signals from the ventricular electrode or electrodes are connected to QRS sense amplifier 24 and T-wave sense amplifier 26, the outputs of which are inputted to control block 20 for processing. Although not shown, it is understood by those of skill in the pacemaker art that the input amplifiers 24, 26 are controlled in terms of sensitivity and timing by control unit 20. Likewise, signals detected in the atrium by electrodes 19 are delivered to P-wave sense amplifier 25, the output of which is connected through to control 20.

Control block 20 suitably incorporates a microprocessor with associated software, the software being stored in memory 21, as indicated. Memory 21 may contain RAM and ROM, and the assignment of pacemaker functions can be divided between hardware and software in any desired manner. In the preferred embodiment of this invention, the algorithms are suitably carried out under software control. One or more sensors 26 may be provided to continuously detect rate-indicating parameters, the parameter signals being inputted to control block 20 to provide rate responsive control, in a known manner. Alternately, as in the preferred embodiment, the rate responsive parameter is QT interval, which is determined by control 20 by timing the duration between a delivered stimulus (VP) and the following T wave. Thus, in the context of this invention, the rate responsive control may suitably vary pacing rate between an upper rate limit (URL) and a lower rate limit (LRL) in a known fashion. It is the adjustment of LRL to a lower value during nighttime that is the focus of this invention. As illustrated at 27, the pacemaker suitably has a transmitter/receiver for receiving programmer communications from an external programmer, and for transmitting collected data back to a transmitter, in a known fashion.

Referring now to FIG. 2, there is shown an illustration of the circadian variation in the QT interval over approximately one day. This graph excludes relatively fast response variations due to exercise, excitement, etc., which are useful for rate responsiveness. As depicted, the QT interval starts at a relatively short interval, corresponding to a reasonable midday degree of patient activity; progresses upwardly to a longer interval, corresponding to lower activity, or nighttime and sleep; and then comes back down again to a relatively shorter daytime interval. Thus, the basic circadian variation in the QT interval is from a shorter value corresponding to daytime to a longer value corresponding to nighttime. It is to be understood additionally that there can be gradual long-term variations in QT interval such as changes due to medication, changes due to illness, seasonal changes, work habit changes, travel-related changes, etc., as well as the normal diurnal and nocturnal variations as represented in this figure. Thus, the preferred algorithms of this invention must take such changes into account, and provide for a continuously updated determination of the nighttime periods when LRL is lowered.

Still referring to FIG. 2, there is illustrated the parameter QT_max, which reflects the long-term average of maximum QT intervals measured daily. When QT intervals are smaller than the QT_max parameter, the pacemaker algorithm causes the parameter to drift towards the smaller intervals, e.g., QT_max=QT_max–drift, where the drift rate is programmable. When QT intervals become longer than the current QT_max, then the parameter is increased, e.g., QT_max=QT_max+delta_1.

Referring now to FIG. 3, there is illustrated a first approach to detecting actual patient sleeping hours, for the purpose of setting night LRL. In order to detect actual sleeping hours, another parameter QT_sleep is introduced as being equal to QT_max minus delta_sleep, as illustrated. The aim is to adapt this parameter so that it initiates start of night and end of night to correspond to a reasonable period of sleep, which reasonable period is indicated by the parameter Night_duration. The parameter Night_duration is determined from the patient history, and inputted by the external programmer into the pacemaker. The parameter QT_sleep is determined to follow QT_max at a fixed delta_sleep distance. When the QT interval becomes longer than the QT_sleep, the patient is assumed to be sleeping and the lower rate limit is decreased; this night value of LRL is maintained for the fixed Night_duration, as illustrated. For an accurate adjustment of QT_sleep to correspond to the patient conditions, the actual period between the time when QT_int rises above QT_sleep and when it drops back down below QT_sleep must correspond closely to night_duration. Where this match is not a good one, delta_sleep can be re-programmed, or a different algorithm can be used.

A first modification of the algorithm can be made to avoid false indication of actual nighttime, i.e., to avoid starting lower LRL when QT_int rises above QT_sleep but does not stay there very long, such as may occur during periods of daytime rest. If it is assumed that at the actual beginning of night, QT interval will remain above QT_sleep for an extended period, e.g., at least 30 minutes, then this period of time can be defined as Night_criterion and used to establish real nighttime. An up-down time counter, for measuring "time_elapsed", is used to determine that the QT interval has been longer than QT_sleep for a selected duration, to filter out the fluctuations around QT_sleep and to avoid false indications of nighttime. Since, in a preferred embodiment, QT interval is measured every cycle, Time_elapsed is adapted, or counted by each cycle time. Thus, when QT_int first rises above QT_sleep, Time_elapsed is counted cycle-by-cycle to determine when the Night_criterion has been met; after this, the Time_elapsed counter is zeroed and then incremented every cycle until Night_duration hours have passed, e.g., 8 hours as illustrated in FIG. 3. Thus, the algorithm provides as follows:

IF (QT_int >QT_sleep),
  then, Time_elapsed=Time_elapsed+cycle_time
  else, Time_elapsed=Time_elapsed–cycle_time IF (Time_elapsed >Night_criterion) AND flag=DAY,
  then flag=NIGHT; decrease LRL IF flag=NIGHT,
  then Time_elapsed=Time_elapsed+cycle_time IF (Time_elapsed >night_duration) AND flag=NIGHT,
  then Flag=DAY; increase LRL.

Figure 3A:
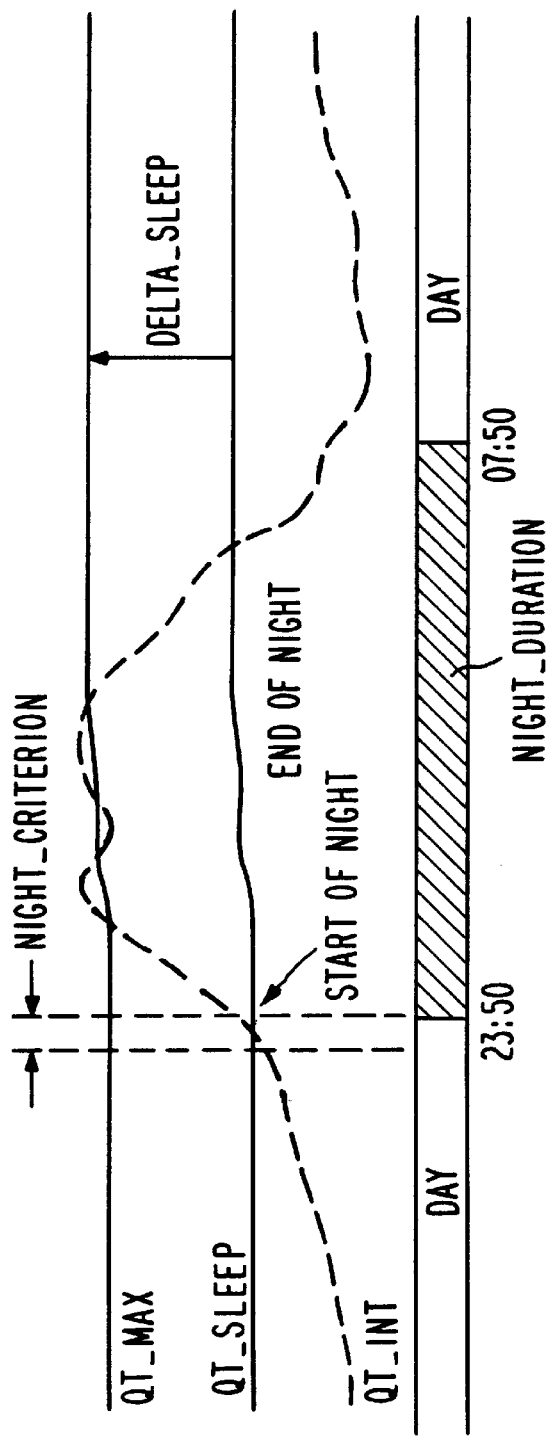
FIG. 3A is a graph illustrating determination of nighttime LRL by the parameters QT_sleep and Night_duration.
Figure 3B:
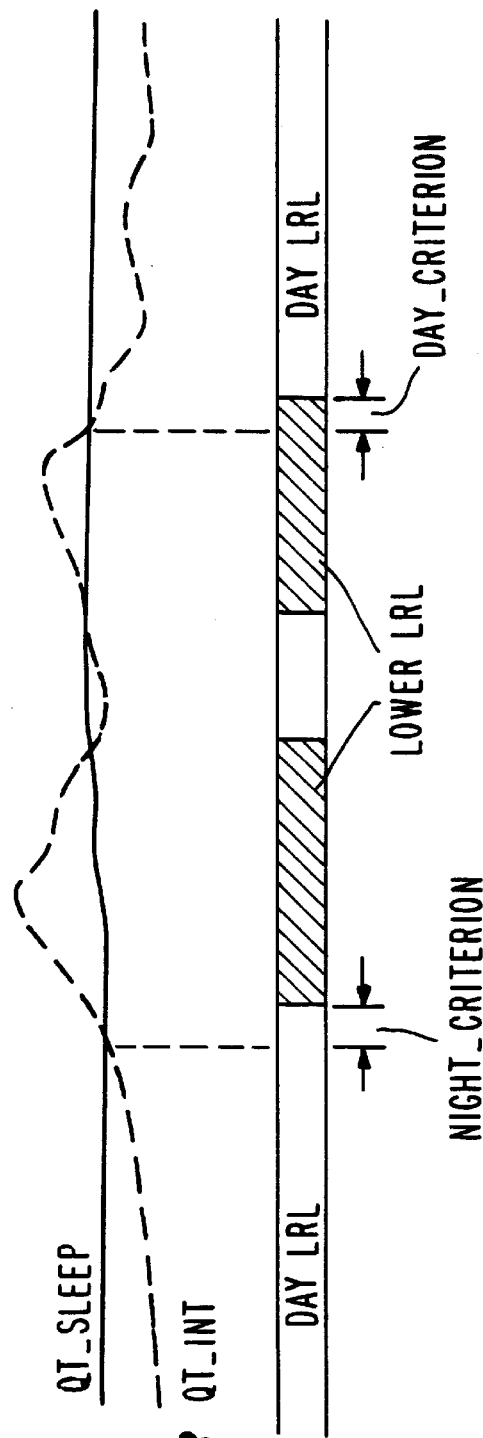
FIG. 3B is a diagram illustrating determination of nighttime LRL by the parameters QT_sleep, night_criterion and day_criterion.

An alternative way to determine the night period for lower LRL is to control the start of Day by QT_sleep as well, as illustrated in FIG. 3B. In this situation, the parameter Day_criterion is introduced, and the Time_elapsed not only determines the start of Night by timing out Night_criterion, but also determines the end of Night, or start of Day, by timing out Day_criterion. At the end of Night, the QT intervals tend to become shorter than QT_sleep, and when this is found to occur for the Day_criterion length of time, e.g., 30 minutes, then Day is determined. Note that the Night_period, which is the accumulated time that Night is thus determined, may not be a continuous period of rest; whenever the trend in QT intervals tends to become longer than QT_sleep, the lower rate limit is raised, but shortening of QT interval for more than the Day_criterion may raise the LRL. Thus, as illustrated in FIG. 3B, there may be several periods, or intervals of night LRL, which results from using QT_sleep to determine end of Night as well as beginning of Night, rather than relying on a fixed Night_duration.

Figure 4A:
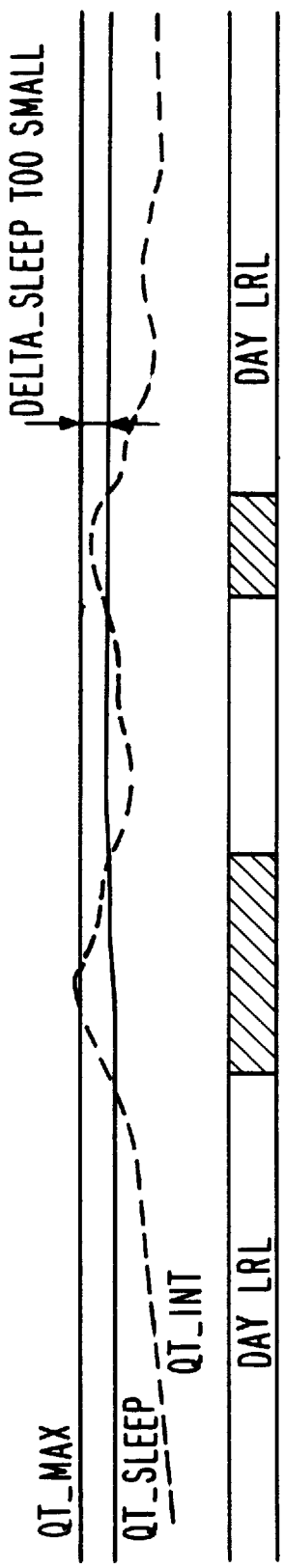
FIG. 4A is a diagram illustrating a situation where the parameter delta_sleep is too small, which would result in a nighttime LRL for too short a duration.
Figure 4B:
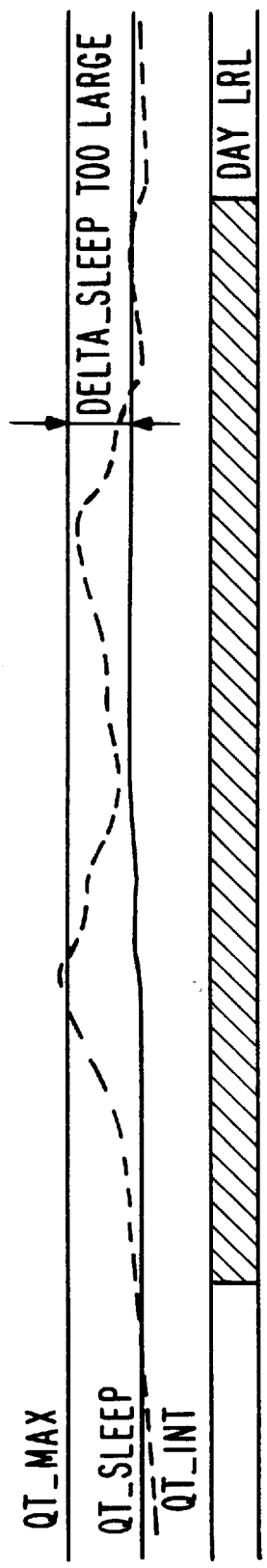
FIG. 4B is a diagram illustrating a situation where the parameter delta_sleep is too large, which would cause too long a nighttime LRL duration.

As illustrated in FIGS. 4A and 4B, the success of this algorithm depends upon appropriate adjustment of QT_sleep. As seen in FIG. 4A, if the delta_sleep is too small, such that QT_sleep is too close to QT_max, then there occur plural relatively short periods of Night LRL, with one or more periods of Day LRL during the patient's actual nighttime. As illustrated in FIG. 4B, if delta_sleep is too large, then night LRL may extend for a longer period than the desired Night_duration, which corresponds to the patient's desired length of sleep. Accordingly, it is seen that delta_sleep either must be programmed accurately to correspond to patient conditions, or must be dynamically adapted.

Figure 5A:
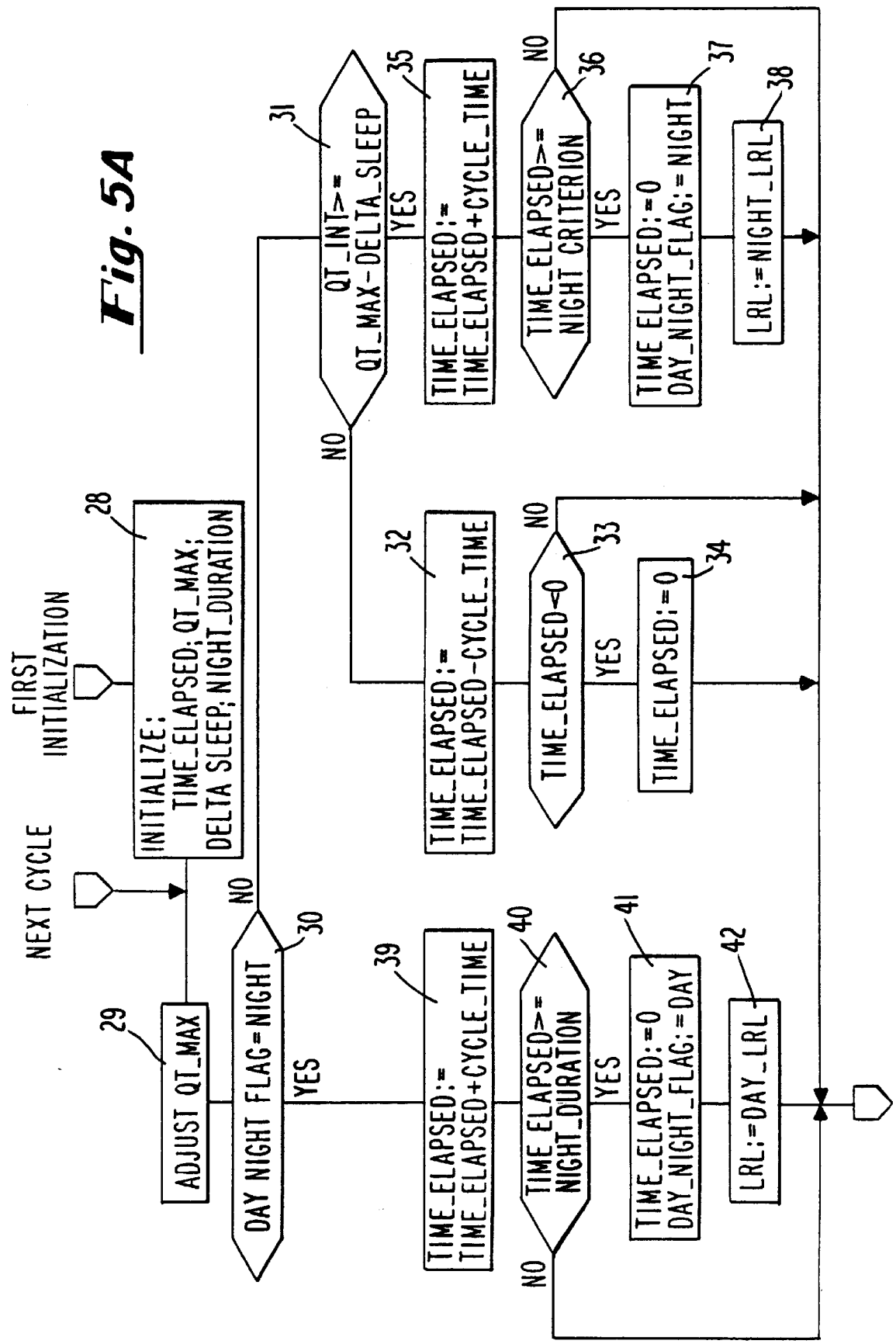
FIG. 5A is a flow diagram of a pacemaker algorithm for determining the nighttime LRL in accordance with the arrangement illustrated in FIG. 3A, where night LRL is determined as a function of QT_sleep and a fixed night_duration.

Referring now to FIG. 5A, there is shown a flow diagram representing the primary steps in the algorithm for adjusting LRL to night and day values corresponding to the arrangement represented in FIG. 3A. At 28, the algorithm is initialized. Thus, values of time_elapsed, QT_max, delta_sleep and night_duration are initialized. At 29, QT_max is adjusted, if required. At 30 it is determined whether the day_night flag is set to NIGHT, ie, is LRL set to the nighttime value. If no, meaning that it is daytime, the routine goes to 31, and determines whether QT_int is greater than or equal to QT_max -delta_sleep (QT_sleep). If no, at 32 time_elapsed is decremented by cycle_time, and then compared to zero at 33; time_elapsed is set equal to zero at 34 if it had been made negative. If the result at 31 is YES, then at 35 time_elapsed is incremented by cycle_time. At 36 it is determined whether time_elapsed has become greater than or equal to Night_criterion. If NO, the routine exits, to start again next cycle; if YES, meaning that night time is to start, at 37 time_elapsed is set to zero, and the flag is set to NIGHT. Then, at 38, LRL is set to the night value, night_LRL.

Returning to block 30, if the flag is not set to NIGHT, ie, it is set to DAY, then the routine goes to 39 and increments time_elapsed by one cycle_time. At 40, it is determined whether time_elapsed has reached Night_duration. If NO, the routine exits; if YES, at 41 time_elapsed is set to zero, and the flag is set to DAY. Then, at 42, LRL is set to the day value, day_LRL, and the routine exits.

Referring now to FIG. 5B, there is shown a flow diagram of the steps taken by a pacemaker in carrying out the arrangement of FIG. 3B. In this embodiment of the invention, the fixed Night_duration is not used, but rather night LRL is started when QT_int is longer than QT_sleep for night_duration, and is ended when QT_int becomes shorter than QT_sleep for day_duration. The first initialization of the routine is done at 44, where time_elapsed; QT_max; and delta_sleep are set; Night_criterion and Day_criterion are values that have been programmed into the pacemaker. Steps 45 thru 54 are exactly the same as, and correspond to steps 29 thru 38 of FIG. 5A, meaning that determination of Night_LRL is the same. If the NIGHT flag has been set, the routine differs from that of FIG. 5A by determining when day_criteria has been timed out. At block 55 it is determined whether QT_int is less than or equal to QT_sleep. If No, at 48, time_elapsed is decremented by cycle_time; at 49 time elapsed is compared to zero, and set equal to zero at 50 if it had been decremented to less than zero. If the answer at 55 is YES, meaning that QT_int has shortened to less than QT_sleep, then the routine goes to 56 and increments time_elapsed by one cycle_time. At 57, time_elapse is compared to Day_criterion; when it has become equal to or greater than Day_criterion, at 58 the flag is set to DAY, and time_elapsed is set to zero. Then, at 59, LRL is set to day_LRL.

Referring now to FIGS. 6A and 6B, there are shown illustrations of another embodiment, wherein the parameter delta_sleep is adjusted on a daily basis as a step to bring the pacemaker-determined night LRL into better correspondence with patient sleep periods, and to match the actual night LRL with the programmed value of night_duration. In this arrangement, start of night, where LRL is shifted to the lower night value, is determined by a variable parameter night_time; and end of night or start of day, is determined by another parameter day_time. The time period between night_time and day_time represents the duration of lower LRL, and is adjusted whenever possible to reflect the length of the detected resting period or periods, which are determined by when QT_int is longer than QT_sleep. In other words, the pacemaker has a stored night_time value, e.g., 11:00 pm, at which time LRL is dropped to its lower value; and a stored day_time value, e.g., 6:30 am, when LRL is set back to its day value. The routine adjusts delta_sleep and measures night periods of QT_int longer than QT_sleep, and shifts the night_time and day_time values when the night period value suggests a shifted circadian rhythm.

Referring specifically to FIG. 6A, there is illustrated a situation where the delta_sleep parameter is reasonably well adjusted. The night periods, where QT interval is longer than QT_sleep, are illustrated. In this case there are two such periods. The parameters night_time and day_time define the period of night LRL, which reasonably matches the night periods of QT interval above QT_sleep, and also reasonably matches the night_duration value. In this arrangement, it can be seen that night_time comes somewhat after the beginning of the first night period, and day_time ends somewhat after the end of the second night period. As a consequence, it is seen that it would be desirable, in order to more accurately track the patient's circadian rhythm, to shift night_time to an earlier moment; the parameter day_time can also be shifted to an earlier moment to more accurately correspond to the end of the last night period. FIG. 6A illustrates a situation where two separate night periods are detected. To obtain a more accurate determination of night period, once the first night period is initiated, QT_sleep may be dropped by a hysteresis value, as shown in FIG. 6B. In this arrangement, a modest middle of the night dip in QT interval does not bring it below the hysteresis value of QT_sleep, such that a continuous night period is determined where QT interval remains above the hysteresis value of QT_sleep. This is useful in the algorithm for adjusting QT_sleep, night_time and day_time, as set forth in FIGS. 7A and 7B.

Figure 7A:
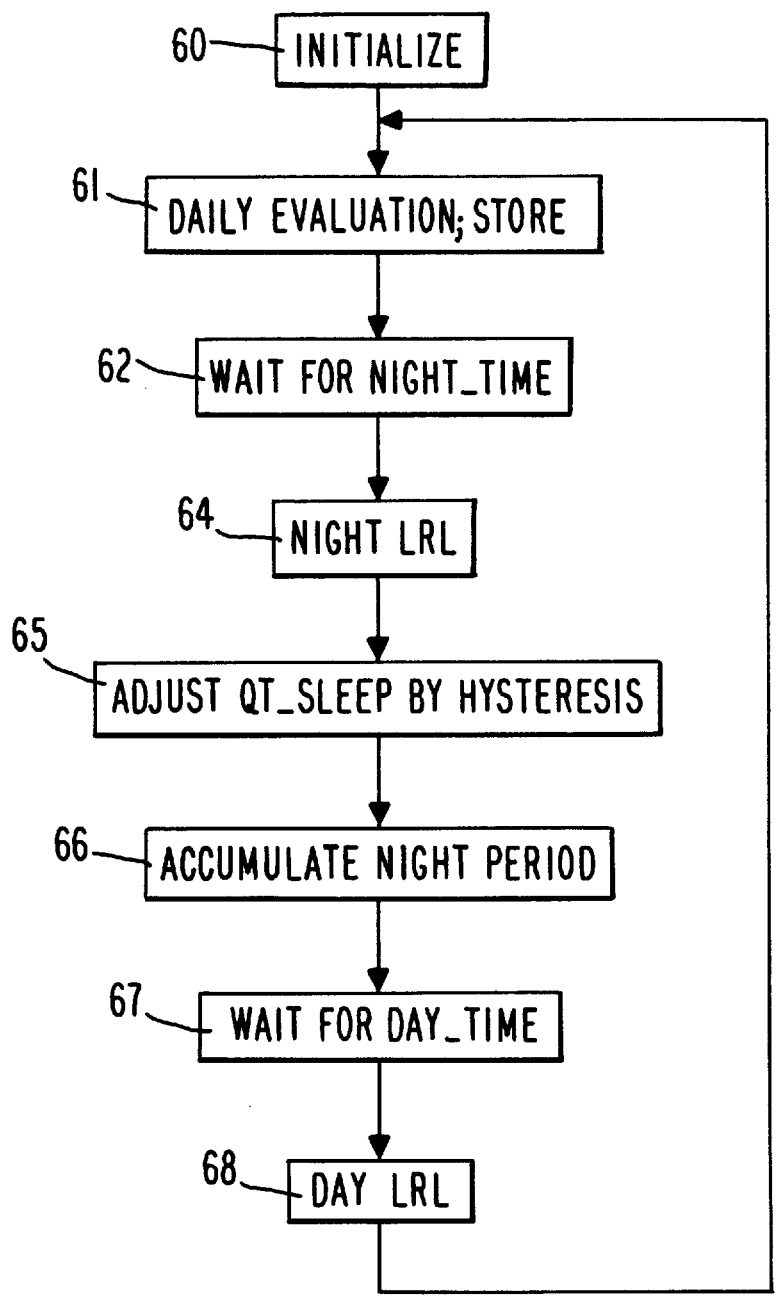
FIG. 7A is a flow diagram of a pacemaker algorithm in accordance with the arrangement illustrated in FIG. 6B for adapting night LRL on a daily basis, to better match the consistently found circadian pattern.

Referring now to FIG. 7A, at step 60 the routine is initialized, meaning that the parameters involved are set to initial values. At 61, a daily evaluation is made, as described more fully in FIG. 7B below, and the results of the evaluation are stored. This evaluation involves varying delta_sleep, and adapting day_time and night_time accordingly. At 62, the pacemaker waits for night_time, and when this occurs night LRL is set, as shown at 64. Following this, at 65 QT_sleep is adjusted by the hysteresis amount. At 66, the routine accumulates the night_period, i.e., determines the total amount of time through the night that QT_interval is longer than QT_sleep. At 67 the pacemaker waits for day_time, and when this timed out at 68 the lower rate limit is set to the day value of LRL.

Referring now to FIG. 7B, there is shown a detailed flow diagram for the daily evaluation of the circadian pattern of the QT_interval. At 66, as discussed in connection with FIG. 7A, the night period is determined, i.e., the accumulated time and whether or not there were multiple periods. At 70, the determined night period is compared to night_duration, which has been programmed to reflect desirable length of nighttime for the patient. If the night period is not much greater than night_duration, the routine goes to 71, and determines whether night period is much less than night_duration. If no, the routine goes to block 72 and determines whether there have been multiple night periods, e.g., as represented in FIG. 6A. If yes, the routine exists, with the conclusion that there is no circadian pattern that can be found, and no adjustment is to be made. Returning to 71, if night period is found to be much less than night_duration, this indicates that delta_sleep is too small, resulting in QT_sleep being too close to QT_max. Consequently, the routine goes to 73 and increases delta_sleep by a predetermined increment, and then exists. Note that as long as the night period is found to be much less than the night_duration, delta_sleep will be incremented on a daily basis until a circadian pattern is found.

Returning to block 70, if the night period is found to be much greater than night_duration, the routine branches to 75 and determines whether multiple night periods have been found. If yes, the routine exists, there having been no circadian pattern found. If there are no multiple night periods, the routine goes to 76 and determines whether delta_sleep is greater than a minimum value referred to as delta_min. If no, then delta_sleep is as small as it can be, and the routine exists. If delta_sleep is greater than delta_min, then the routine goes to 77 and decreases delta_sleep. This adaptation is continued until a circadian pattern is found with night period more in line with night_duration.

Returning to block 72, if it is determined at that point that there are no multiple night periods, then the conclusion is that the night period substantially matches night_duration. The aim then is to check further to see if there should be a shift of either night_time or day_time. At 78, it is determined whether the start of the night period is substantially the same as the parameter night_time. If no, the routines adjusts night_time at 79, moving it incrementally toward the start of the night period. At 80, it is determined whether the end of the night period is substantially coincident with the parameter day_time. If no, then at 81 the routine adjusts day_time toward the end of the night period. By this means, both day_time and night_time, or just one of them, can be adjusted to correspond to the night period, the night period in turn having been affected by adjustments in delta_sleep. LRL is thus adapted to changes in the patient's circadian rhythm.

It is to be recognized that the pacemaker system and method of this invention can be adapted to change additional pacing control criteria. Thus, the pacemaker may have the capability of operating in a hysteresis mode, where the pace pulse escape interval has a hysteresis value. Depending on the stored data from the daily evaluations, hysteresis may be adopted or varied for nighttime pacing, along with the lowered LRL. Any other criteria for controlling pacing may also be modified on a nighttime-daytime basis. The accumulated data can also be used for other updating, such as adjusting programmed values such as night_duration.

I claim:

1. A pacemaker for generating pace pulses for delivery to a patient, the pacemaker having a pulse generator, sensing means for sensing a parameter which has a circadian variation characterized by nighttime change in a first direction and daytime change in a second direction, control means for controlling pacing rate, and comprising LRL means for controlling the lower rate limit at which said pace pulses are generated, said LRL means having:

first means for determining a first value of said parameter which is a measure of the recent extreme value of said parameter in said first direction, second means for setting a night value of said parameter, third means for determining night conditions as a function of when said parameter is between said night value and said first value, and adjusting means for adjusting said lower rate limit to a lower night value during said night conditions.

2. The pacemaker as described in claim 1, wherein said sensing means senses the QT interval following delivered pace pulses, whereby said parameter is QT interval.

3. The pacemaker as described in claim 2, wherein said first means comprises means for determining a value representative of maximum QT interval, and said second means has means for setting said night value to a QT interval value which is less than said maximum QT interval.

4. The pacemaker as described in claim 3, wherein said third means comprises means for determining when said QT interval increases from a value less than said night value to a value more than said night value.

5. The pacemaker as described in claim 4, wherein said third means comprises means for determining start of a night condition based on said QT interval maintaining a value greater than said night value for a predetermined time.

6. The pacemaker as described in claim 1, comprising duration means for storing a time duration corresponding to desired sleep duration, and wherein said third means comprises means determining end of a night condition when a said night condition has extended for said time duration.

7. The pacemaker as described in claim 6, comprising means for adjusting said duration measure as a function of patient history.

8. A rate responsive implantable pacemaker, having pace pulse generator means for generating pace pulses, rate control means for controlling the rate of generated pace pulses, QT means for continuously determining QT values, and rate limit means for setting a lower rate limit on said pace pulse rate, comprising:

QT max means for obtaining a measure of the daily maximum value of QT, night means for determining a start of night as a function of QT variations relative to said maximum value, and said rate means having LRL means for normally maintaining a lower rate limit at a first value, and for adjusting said lower rate limit to a lower value at said start of night.

9. The pacemaker as described in claim 8, comprising timing means for timing out a night duration, and wherein said LRL means comprises day means for setting said lower rate limit to said first value upon timing out said night duration.

10. A rate responsive implantable pacemaker for pacing a patient's heart, having pace pulse generator means for generating pace pulses, rate control means for controlling the rate of generated pace pulses, QT means for continuously determining the value of a QT interval, and rate limit means for setting a lower rate limit on said pace pulse rate, comprising:

start night means for setting said lower rate limit to a lower night value at a first adjustable time, end night means for setting said lower rate limit to a higher value at a second adjustable time, and adjusting means for adjusting both of said first and second times as a function of variations of said QT interval.

11. The pacemaker as described in claim 10, further comprising QT max means for obtaining a measure of the daily maximum value of QT, sleep means for determining a sleep value of QT which is shorter than said maximum value by a given amount, duration means for determining the duration of time each night that QT is longer than said sleep value, and wherein said adjusting means adjusts said first and second times as a function of said nightly time duration.

12. A method of controlling the available pacing rate of a pacemaker implanted in a patient so as to adapt to nighttime conditions, comprising:

controlling pacing during daytime conditions with a first set of criteria;

determining a nighttime duration, and controlling pacing during said nighttime duration with a second set of criteria;

sensing a QT interval which varies with the patient's circadian rhythm, and accumulating data representative of variations of said QT interval;

determining from said accumulated data information representative of the patient's circadian rhythm; and adjusting said nighttime duration as a function of said information.

13. The method as described in claim 12, wherein said first set of criteria comprises a day lower rate limit, and said second set of criteria comprises a night lower rate limit.

14. The method as described in claim 12, wherein said second criteria comprises a nighttime hysteresis escape interval.

15. The method as described in claim 12, comprising evaluating said accumulated data daily, and adjusting said nighttime duration whenever a said daily evaluation indicates that said duration can be adjusted to better match the patient's circadian rhythm.

16. The method as described in claim 15, comprising setting a start of said nighttime duration and an end of said nighttime duration, and wherein said adjusting comprises shifting either said start or end.

17. A rate responsive pacemaker having a pulse generator for generating pace pulses, and rate control means for controlling the rate of said generated pace pulses in accordance with a set of rate criteria, comprising:

parameter means for continuously determining a parameter which varies with the patient's circadian rhythm, data means for collecting and storing data representative of nighttime variations of said determined parameter, and adapting means for adapting said rate criteria as a function of said stored data.

18. The pacemaker as described in claim 17, wherein said rate control means comprises means for setting a night lower rate limit, and said adapting means adapts said night lower rate limit.

19. The pacemaker as described in claim 18, wherein said parameter means comprises QT means for determining QT interval, and said data means has means for collecting and storing data representative of daily maximum value of QT interval.

* * * * *